(12) United States Patent
Brown et al.

(10) Patent No.: US 12,116,618 B2
(45) Date of Patent: *Oct. 15, 2024

(54) USE OF APTAMERS IN PROTEOMICS

(71) Applicant: Caris Science, Inc., Irving, TX (US)

(72) Inventors: Clive Gavin Brown, Cambridge (GB); Koen Kas, Schilde (BE); Sven Agnes Jan Eyckerman, Nazareth (BE)

(73) Assignee: Caris Science, Inc., Irving, TX (US)

( * ) Notice: Subject to any disclaimer, the term of this patent is extended or adjusted under 35 U.S.C. 154(b) by 733 days.

This patent is subject to a terminal disclaimer.

(21) Appl. No.: 17/222,772

(22) Filed: Apr. 5, 2021

(65) Prior Publication Data

US 2022/0002780 A1 Jan. 6, 2022

Related U.S. Application Data

(63) Continuation of application No. 16/406,903, filed on May 8, 2019, now Pat. No. 10,995,360, which is a continuation of application No. 15/669,782, filed on Aug. 4, 2017, now Pat. No. 10,316,349, which is a continuation of application No. 14/477,907, filed on Sep. 5, 2014, now Pat. No. 9,758,811, which is a continuation of application No. 12/682,537, filed as application No. PCT/GB2008/003447 on Oct. 10, 2008, now abandoned.

(30) Foreign Application Priority Data

Oct. 12, 2007 (EP) ..................................... 07020049

(51) Int. Cl.
| | | |
|---|---|---|
| C12Q 1/6804 | (2018.01) | |
| C12N 15/11 | (2006.01) | |
| C12N 15/115 | (2010.01) | |
| G01N 33/68 | (2006.01) | |

(52) U.S. Cl.
CPC .......... C12Q 1/6804 (2013.01); C12N 15/111 (2013.01); C12N 15/115 (2013.01); G01N 33/6818 (2013.01); C12N 2310/16 (2013.01); C12N 2320/11 (2013.01)

(58) Field of Classification Search
CPC . C12N 15/111; C12N 15/115; C12N 2310/16; C12N 2320/11; C12Q 1/6804
USPC ............. 435/6.1, 91.1, 91.31; 536/23.1, 24.5
See application file for complete search history.

(56) References Cited

U.S. PATENT DOCUMENTS

| | | | |
|---|---|---|---|
| 5,434,064 A | 7/1995 | Schlessinger | |
| 6,309,822 B1 | 10/2001 | Fodor et al. | |
| 7,074,586 B1 | 7/2006 | Cheronis et al. | |
| 9,758,811 B2* | 9/2017 | Brown | C12Q 1/6804 |
| 10,316,349 B2 | 6/2019 | Brown et al. | |
| 10,361,349 B2* | 7/2019 | Andrews | H01L 33/60 |
| 10,995,360 B2* | 5/2021 | Brown | C12Q 1/6804 |
| 2003/0087239 A1 | 5/2003 | Stanton | |
| 2003/0143580 A1 | 7/2003 | Straus | |
| 2003/0219801 A1 | 11/2003 | Lipshutz | |
| 2005/0142582 A1 | 6/2005 | Doyle | |
| 2005/0123939 A1 | 7/2005 | Gorenstein et al. | |
| 2006/0211044 A1 | 9/2006 | Green | |
| 2007/0166741 A1 | 7/2007 | Heil et al. | |
| 2007/0172873 A1 | 7/2007 | Brenner | |
| 2009/0305254 A1 | 12/2009 | Sode et al. | |
| 2010/0111768 A1 | 5/2010 | Banerjee et al. | |
| 2010/0304991 A1 | 12/2010 | Brown | |

FOREIGN PATENT DOCUMENTS

| | | |
|---|---|---|
| EP | 2209893 | 11/2013 |
| JP | 2007-014292 | 1/2007 |
| JP | 2009/532031 | 9/2009 |
| JP | 5766948 | 8/2015 |
| WO | WO 00/06770 | 2/2000 |
| WO | WO 2005/003291 | 1/2005 |
| WO | WO 2005/049826 | 6/2005 |
| WO | WO 2005/071110 | 8/2005 |
| WO | WO 2006/128010 | 11/2006 |
| WO | WO 2007/032359 | 3/2007 |
| WO | WO 2007/044071 | 4/2007 |
| WO | WO 2007/086403 | 8/2007 |
| WO | WO 2007/123744 | 11/2007 |
| WO | WO 2009/047526 | 4/2009 |

OTHER PUBLICATIONS

Anderson et al., "Quantitative mass spectrometric multiple reaction monitoring assays for major plasma proteins," Mol. Cell Prot., 2006, 5(4):573-588.
Bennet, "Array of hope for personalized medicine," Current Drug Discovery; Feb. 2004, pp. 15-19.
Berezovski et al., "Affinity Analysis of a Protein-Aptamer Complex Using Nonequilibrium Capillary Electrophoresis of Equilibrium Mixtures," Analytical Chemistry, 2003, 75:1382-1386.
Berezovski et al., "Nonequilibrium capillary electrophoresis of equilibrium mixtures—a single experiment reveals equilibrium and kinetic parameters of protein-DNA interactions," Journal of the American Chemical Society, 2002, 124(46):13674-13675.
Bio-IT World. Solexa History. 2010. Available at http://www.bio-itworld.com/2010/issues/sept-oct/solexa.html.

(Continued)

*Primary Examiner* — Jane J Zara
(74) *Attorney, Agent, or Firm* — Kilpatrick Townsend & Stockton LLP

(57) ABSTRACT

The present invention is a method for measuring the amount of at least one molecule in a biological sample, the method comprising a) combining the sample, or a derivative thereof, with one or more aptamers and allowing one or more molecules in the sample to bind to the aptamer(s); b) separating bound from unbound molecules; and c) quantifying the molecule(s) bound to the or each aptamer, wherein quantification of the bound molecule(s) is carried out by sequencing at least part of the or each aptamer. Uses of and products derived from the method are also contemplated.

20 Claims, 9 Drawing Sheets

(56) References Cited

OTHER PUBLICATIONS

Branton et al., "The potential and challenges of nanopore sequencing," 26:1146-1153 (2008).
Brenner et al., "Gene expression analysis by massively parallel signature sequencing (MPSS) on micro bead arrays," Nat Biotechnol. 2000, 18(6):630-4.
Cerchia et al., "Minireview: Nucleic acid aptamers in cancer medicine," FEBS Letters, 2002, 528: 12-16.
Cho et al., "Optimization of aptamer microarray technology for multiple protein targets," Analytica Chimica Acta, 2006, 564: 82-90.
CN Patent application No. 200880120684.1, Notification of Reexamination (English Translation) dated Feb. 14, 2016.
CN Patent application No. 201310045505.5 (divisional of CN200880120684.1 ), First Office Action (English Translation) dated Jun. 18, 2014.
CN Patent application No. 201310045505.5, Decision to Grant (English Translation at pp. 3-5) dated Oct. 18, 2016.
CN Patent application No. 201310045505.5, Fourth Office Action (English Translation) dated Jun. 20, 2016.
CN Patent application No. 201310045505.5, Second Office Action (English Translation) dated Dec. 24, 2014.
CN Patent application No. 201310045505.5, Third Office Action (English Translation) dated Nov. 2, 2015.
Drabovich et al., "Selection of smart aptamers by methods of kinetic capillary electrophoresis," Anal. Chem., 2006, 78(9):3171-8.
Elrick et al., "Proteomics: Recent Applications and New Technologies," Basic & Clinical Pharmacology & Toxicology, 2006, 98(5):432-441.
EP Patent 2209893 B1, Decision rejecting the opposition, dated Jun. 27, 2016.
EP Patent 2209893 B1, Minutes of the oral proceedings before the Examination Division, dated Jun. 27, 2016.
EP Patent 2209893 B1, Termination of the opposition, dated Oct. 7, 2016.
EP Patent application No. 08837175.2, Decision to Grant (European Patent No. 2209893) dated Oct. 24, 2013.
EP Patent application No. 08837175.2, Intention to Grant dated Feb. 15, 2013.
EP Patent application No. 08837175.2, Search Report dated Aug. 22, 2012.
EP Patent No. 2209893, Notice of Opposition to a European Patent dated Aug. 20, 2014.
EP Patent No. 2209893, Opposition Result (opposition rejected I patent upheld) dated Jun. 7, 2016.
EP Patent No. 2209893, Summons to Attend Oral Proceedings re Opposition dated Jul. 16, 2015.
EP Patent No. 2209893, Supplemental Submission re Opposition dated May 4, 2016.
Fan et al., "Highly Parallel Genomic Assays," Nature Reviews, Genetics, 2006, 7(8):632-644.
Illumina—Specification Sheet: Illumina® Sequencing Genome Analyzer System. 2007. Available at web.archive.org/web/20071011095455/http://www.illumina.com/downloads/GenomeAnalyzerSpecSheet.pdf.
Illumina Solexa presentation filed with the U.S. Securities and Exchange Commission. 2006. Available at www.sec.gov/Archives/edgar/data/913275/000095012306014236/0000950123-06-014236-index.htm.
Illumina® Systems & Software—Technology Spotlight; "DNA Sequencing with Solexa Technology" 2007. Available at: web.archive.org/web/20071011095600/http://www.illumina.com/downloads/SS_DNAsequencing.pdf.
International Preliminary Report on Patentability for PCT/GB2008/003447, issued Apr. 13, 2010.
JP Patent application No. 2010-528482, Decision to Grant dated May 19, 2015.
JP Patent application No. 2010-528482, Notification ofReason(s) for Refusal dated Sep. 30, 2014. English translation at pp. 6-10.
Kasschau et al., "Genome-wide profiling and analysis of *Arabidopsis* siRNAs," PLoS Biol, 2007, 5(3):e57.
Kulbachinskiy, "Methods for Selection of Aptamers to Protein Targets", Biochemistry, 73:1505-1518 (2007).
Lee et al., "Biomarker Assay Translation from Discovery to Clinical Studies in Cancer Drug Development: Quantification of Emerging Protein Bio markers," Adv Cancer Res, 2007, 96:269-98.
Liu et al., "A model for random sampling and estimation of relative protein abundance in shotgun proteomics," Anal. Chem., 2004, 76(14):4193-201.
Illumina Corporation webpage: illumina and solexa-finding the answers together. 2007. Available at web.archive.org/web/20070603161104/http://www.illumina.com/pagesnm.ilmn?ID=222.
Lu et al., "Elucidation of the Small RNA Component of the Transcriptome," Science, 2005, 309(5740):1567-9.
Margulies et al., "Genome Sequencing in Microfabricated High-Density Picolitre Reactors," Nature, 2005, 437(7057):376-380.
Ng et al., "Multiplex Sequencing of Paired-End Ditages (MS-PECT): A Strategy For The Ultra-High-Throughput Analysis of Transcriptomes and Genomes," Nucleic Acids Research, Jul. 2006, 34(12):e84, 10 pages.
Office Action for Chinese Application No. 200880120684.1, (with English translation).
Parameswaran et al., "A pyrosequencing-tailored nucleotide barcode design unveils opportunities for large-scale sample multiplexing," Nucleic Acids Res, 2007, 35(19):e130.
Pohl and Shih, "Principle and applications of digital PCR," Expert Rev Mol Diagn, 2004, 4(1):41-7.
Qian et al., "Advances and challenges in liquid chromatography-mass spectrometry-based proteomics profiling for clinical applications," Mol. Cell. Prot., 2006, 5(10):1727-1744.
Reinarlz et al., "Massively parallel signature sequencing (MPSS) as a tool for in-depth quantitative gene expression profiling in all organisms," Brief Funct Genomic Proteomic, 2002, 1(1):95-104.
Rifai et al., "Protein biomarker discovery and validation: the long and uncertain path to clinical utility," Nature Biotech, 2006, 24(8):971-83.
Robinson and Smyth, "Moderated statistical tests for assessing differences in tag abundance," Bioinformatics, 2007, 23(21):2881-7.
Ruby et al., "Large-scale sequencing reveals 21U-RNAs and additional microRNAs and endogenous siRNAs in C.elegans," Cell, 2006, 127:1193-1207.
Schrattenholz et al., "What does it need to be a biomarker? Relationships between resolution, differential quantification and statistical validation of protein surrogate biomarkers," Electrophoresis, 2007, 28(12):1970-9.
Shendure et al., "Advanced sequencing technologies: methods and goals," Nat Rev Genet, 2004, 5(5):335-44.
Solexa Application Note: DNA Sequencing. 2006. Available at www.ebiotrade.com/custom/upload/news/solexa-.pdf.
Solexa Genome Analysis System brochure. 2006. Available at web.archive.org/web/20061225020204/http://www.solexa.com/pdfs/System%20Profile_10_6_06.pdf.
Solexa webpage "Advancing genetic analysis." 2005. Available at web.archive.org/web/20051224140319/http://www.solexa.com/wt/page/index.
Traverso et al., "Detection of proximal colorectal cancers through analysis of faecal DNA," Lancet, 2002, 359:403-404.
Velculescu et al., "Gene Expression Analysis Goes Digital", Nature Biotechnology, 25(8):878-880 (2007).
Webster's Third New International Dictionary, Definition of "carry out," Gove, eds., 1993, p. 344.
Wiegand et al., "High-affinity oligonucleotide ligands to human IgE inhibit binding to Fc epsilon receptor I," J. Immunol., 1996, 157(1):221-230.
Zangar et al., "ELISA microarray technology as a high-throughput system for cancer biomarker validation," Exp. Rev. Prot., 2006, 3(1):37-44.
Zhang et al., "Ultrasensitive Detection of Proteins by Amplification of Affinity Aptamers," Angew Chem Int Ed Engl, 2006, 45(10): 1576-80.

(56) References Cited

OTHER PUBLICATIONS

Zolg, "The proteomic search for diagnostic biomarkers: lost in translation?," Mol. Cell Prot., 2006, 5(10):1720-1726.

* cited by examiner

USE OF APTAMERS IN PROTEOMICS

CROSS REFERENCE

This application is a continuation of U.S. application Ser. No. 16/406,903, filed May 8, 2019, which is a continuation of U.S. application Ser. No. 15/669,782, filed Aug. 4, 2017; now U.S. Pat. No. 10,316,349, which is a continuation of U.S. application Ser. No. 14/477,907, filed Sep. 5, 2014, now U.S. Pat. No. 9,758,811; which application is a continuation of U.S. application Ser. No. 12/682,537, filed Apr. 9, 2010 and now abandoned; which application is a 371 National Stage filing of International Patent Application Serial No. PCT/GB2008/003447, filed Oct. 10, 2008; which claims priority based on Patent Application No. EP 07020049.8, filed Oct. 12, 2007; the contents of all of which are incorporated herein by reference in their entirety.

BACKGROUND OF THE INVENTION

The proteome is usually described as the entire complement of proteins found in a biological system, such as, e.g., a cell, tissue, body fluid, organ or organism. The study of naturally occurring proteins is generally termed 'proteomics' and encompasses study of the proteome expressed at particular times and/or under internal or external conditions of interest. Proteomics approaches frequently aim at global analysis of the proteome and require that large numbers of proteins, e.g., hundreds or thousands, can be routinely resolved, identified and quantified from a single or multiple sample(s).

Among the promises of proteomics is its ability to recognise new biomarkers, i.e., proteins as biological indicators that signal a changed physiological state, for example due to a disease or a therapeutic intervention. Biomarker discovery usually involves comparing proteomes expressed in distinct physiological states and identifying proteins whose occurrence or expression levels consistently differ between the physiological states (Schrattenholz A, Groebe K. Electrophoresis. (2007) Jun 28(12) 1970-9).

Proteins in blood are a particular target for the identification of markers of disease states and drug treatments. It is widely assumed that the amounts and/or conformation of proteins in the blood should be statistically related to such states in a manner that outweighs intrinsic natural variability. Blood and other body fluids are a particular target because they bathe affected tissues, transport vital proteins and can be obtained for testing using relatively cheap and straightforward procedures during a medical consultation.

However, proteins in blood have a very large range of concentrations, with a small number of proteins accounting for over 99.9% of all proteins and the rest occupying a distribution from picogram to milligram per millilitre (Qian W. J. et al., Mol. Cell. Prot. (2006) 5(10) 1727-1744). Due to the limitations of existing proteomics techniques, this abundance range remains hypothetical. Proteomics scientists have employed a variety of methods to reach into this range, with the aim of also minimizing disruption to the relative abundances of the proteins. This often requires the exclusion of the high-abundance proteins by selective purification. Attempts have also been made to reduce the complexity of the peptides obtained by selectively focusing in on subsets of all peptides in the sample. These procedures are lengthy and the reproducibility between samples, replicates, machines and laboratories has yet to be demonstrated in a manner that would be a pre-requisite for the statistical discovery of biomarker proteins.

Conventional Mass Spectrometry (MS)-based proteomics, commonly used in biomarker discovery, proceeds by separating biological samples to isolate single proteins from the mixture under investigation. More recently, this has advanced from 2D-gels to multi-dimensional column-based high performance liquid chromatography (HPLC). Proteins can be broken down into shorter subunits or peptides. Isolated peptides are then fed into a mass spectrometer that ionises the peptides and breaks them up further, yielding a ladder of mass/charge measurements. These measurements and their abundances can also be quantified under a variety of schemes, usually relative to some control. The resulting ladder of spectra is then interpreted against known peptide sequences or blindly from raw data and the obtained mass and sequence information is used to search sequence databases to identify the proteins from which the respective peptides originated.

However, proteolysis of complex biological samples usually produces hundreds of thousands of peptides which may overwhelm the resolution capacity of known chromatographic and MS systems, causing incomplete resolution and impaired identification of the constituent peptides. Typically in MS-based proteomics, as many as 80% of the spectra derived from the sample cannot be accurately or consistently re-interpreted into discriminatory peptides or thence proteins. Their fragmentation behaviour and abundance in the MS process can also be context dependent, further complicating reproducibility (Liu H, Sadygov R G, Yates J R 3rd. Anal. Chem. (2004) Jul 15 76(14) 4193-201).

One method to enable proteomic analysis of biological samples is to reduce the complexity of peptide mixtures generated by separation of such samples, before subjecting said peptide mixtures to downstream resolving and identification steps, such as chromatographic separation and/or Mass Spectrometry (MS). Ideally, reducing the complexity of protein peptide mixtures will decrease the average number of distinct peptides present per individual protein of the sample, yet will maximise the fraction of proteins of the sample actually represented in the peptide mixture.

The use of blood (serum or plasma) is further obscured by biological processing of proteins in a variety of ways that confound MS-based ascertainment (Ciao W. J. et Mol. Prot. (2006) 5(10) 1727-1744). Recent studies have shown wildly contradictory attempts to identify and count proteins from clinical samples. The very act of isolating, fragmenting and measuring proteins in conventional MS-based proteomics alters their relative abundance and chemical makeup.

The output of proteomics-based analysis is a "hit list" of proteins that are significantly correlated in the samples under study. Typically, this list is a selection of proteins of variable statistical significance. A biologically oriented study of the list is usually made and a rational choice is made about the potential biological significance of each member. The process of reaching a list of hypothetical biomarkers, or proteins of putative statistical significance, is generally called 'Discovery.'

Efforts are then focused on verifying and validating a small number of chosen "hits." This involves confirmation of the measured protein abundances in a broader population of clinical samples with the objective being to show that the discovered and chosen proteins are genuine and not false positives and that they are specific to the disease or drug state. This process of confirming the quantitative significance of a proteomics measurement and putative biomarker in a more generalised population is usually referred to as 'Validation' (Zolg, Mol. Cell Prot. (2006) 5(10), 1720-1726). Often this requires the use of an alternative technology to the discovery phase.

Typically, this is achieved using antibodies raised to the purified putative proteins. These antibodies can then be used in an ELISA-based assay against hundreds of samples, the relevant statistics reapplied and the validity of the protein as a biomarker established. The ultimate intention of this process is also for the antibody to become part of a clinical assay. However, antibodies are time-consuming and costly to produce and it is not always possible to raise an antibody specific to a given protein. A further complication is the presence of alternative variants of the protein or isoforms that may have crusts of attached sugar molecules and other modifications on their surface. Isoforms may not be evident in the Discovery phase MS based identification and thus complicate the statistical significance of the measurements as well as the raising of specific antibodies (Zolg, Mol. Cell Prot. (2006) 5(10), 1720-1726; Rifai et al, Nature Biotech (2006) 24(8) 971-83).

Both Discovery and Validation have high failure rates and are time consuming and costly exercises. Success and failure can usually only be judged after the Validation stage after much time and financial expenditure. Therefore, recent efforts have focused on the refinement of MS-based approaches for discovery and on the bulk generation of antibodies in an effort both to accelerate Discovery, Validation and to derive a clinical product (Anderson and Hunter, Mol. Cell Prot. (2006) 5(4) 573-588; Zangar et al., Exp. Rev. Prot. (2006) 3(1) 37-44).

Accordingly, there is a clear need for new methods to interrogate proteins, particularly complex mixtures of proteins, derived from body fluids. Specifically, there is a need for a technology to identify and measure the abundance of proteins, especially abundance of multiple proteins in a complex mixture, that overcomes the technical drawbacks and scientific and cost constraints that hampers current technology. In particular, tools are needed to replace the costly and sometimes unreliable generation and use of antibodies to identify and validate target proteins. Such tools can also be used to supplant existing Discovery based techologies such as MS, provided a sufficient diversity of antibody alternatives can be generated quickly and cheaply enough, to probe the full range of native proteins in a biological sample.

A clear desideratum for such a tool is minimal manipulation of the mixture so that a true representation of the proteins in their native configuration, together with any natural modification and variations, in the sample may be obtained. Such a tool should also be highly and accurately reproducible.

Aptamers are short polymers, usually nucleic acids (DNA, RNA, PNA), that form well-defined three dimensional shapes, allowing them to bind target molecules in a manner that is conceptually similar to antibodies. Aptamers combine the optimal characteristics of small molecules and antibodies, including high specificity and affinity, chemical stability, low immunogenicity, and the ability to target protein-protein interactions. In addition to high specificity, aptamers have very high affinities to their targets. Typically, aptamers generated against proteins have affinities in the picomolar to low nanomolar range. In contrast to monoclonal antibodies, aptamers are chemically synthesized, rather than biologically expressed, offering a significant cost advantage.

While aptamers provide a useful and effective alternative to antibodies, there still remains a problem on how to quantify proteins, via aptamers. Complex mixtures of proteins and the large dynamic range of proteins present in biological samples provide a particular problem. Typically, aptamers are quantified using radiolabels. While quantification of radiolabels is acceptable, and has been for a number of years, there remains a need to improve and expedite quantification, as well as improve accuracy and reproducibility.

INCORPORATION BY REFERENCE

All publications, patents and patent applications mentioned in this specification are herein incorporated by reference to the same extent as if each individual publication, patent or patent application was specifically and individually indicated to be incorporated by reference.

SUMMARY OF THE INVENTION

The present invention relates to the identification and quantification of proteins in a complex mixture. In particular, the invention relates to the use of aptamers as tags or proxies for proteins and protein quantities in a complex mixture. In another aspect the invention relates to the use of next generation polynucleotide sequencing methods in proteomics.

The present invention relates to a method for measuring the amount of at least one molecule in a biological sample, the method comprising:
  a) combining the sample, or a derivative thereof, with one or more aptamers and allowing one or more molecules in the sample to bind to the aptamer(s);
  b) separating bound from unbound molecules; and
  c) quantifying the molecule(s) bound to the or each aptamer,
  wherein quantification of the bound molecule(s) is carried out by sequencing at least part of the or each aptamer.

BRIEF DESCRIPTION OF TUE DRAWINGS

The figures which follow serve to illustrate the invention in more detail but do not constitute a limitation thereof.

FIG. 1 illustrates the method of the present invention, in which a library of aptamer sequences is mixed with serum proteome. The bound aptamer/protein fraction is eluted before being sequenced and counted on a second generation sequencer. The output from the sequencer is the number of each sequence present in the bound fraction.

FIG. 2 illustrates use of the method for biomarker discovery, in which proteomes from different patients are compared with a baseline or control.

FIG. 3 illustrates an alternative embodiment of the present invention, in which a library of aptamers is mixed with a first serum proteome sample. After quantification of the bound fraction, the population of aptamers binding to proteins of interest within the serum sample is amplified and mixed with a second serum proteome sample. A comparison of the first and second respective quantification outputs is then made.

DETAILED DESCRIPTION OF THE INVENTION

Figure 1:
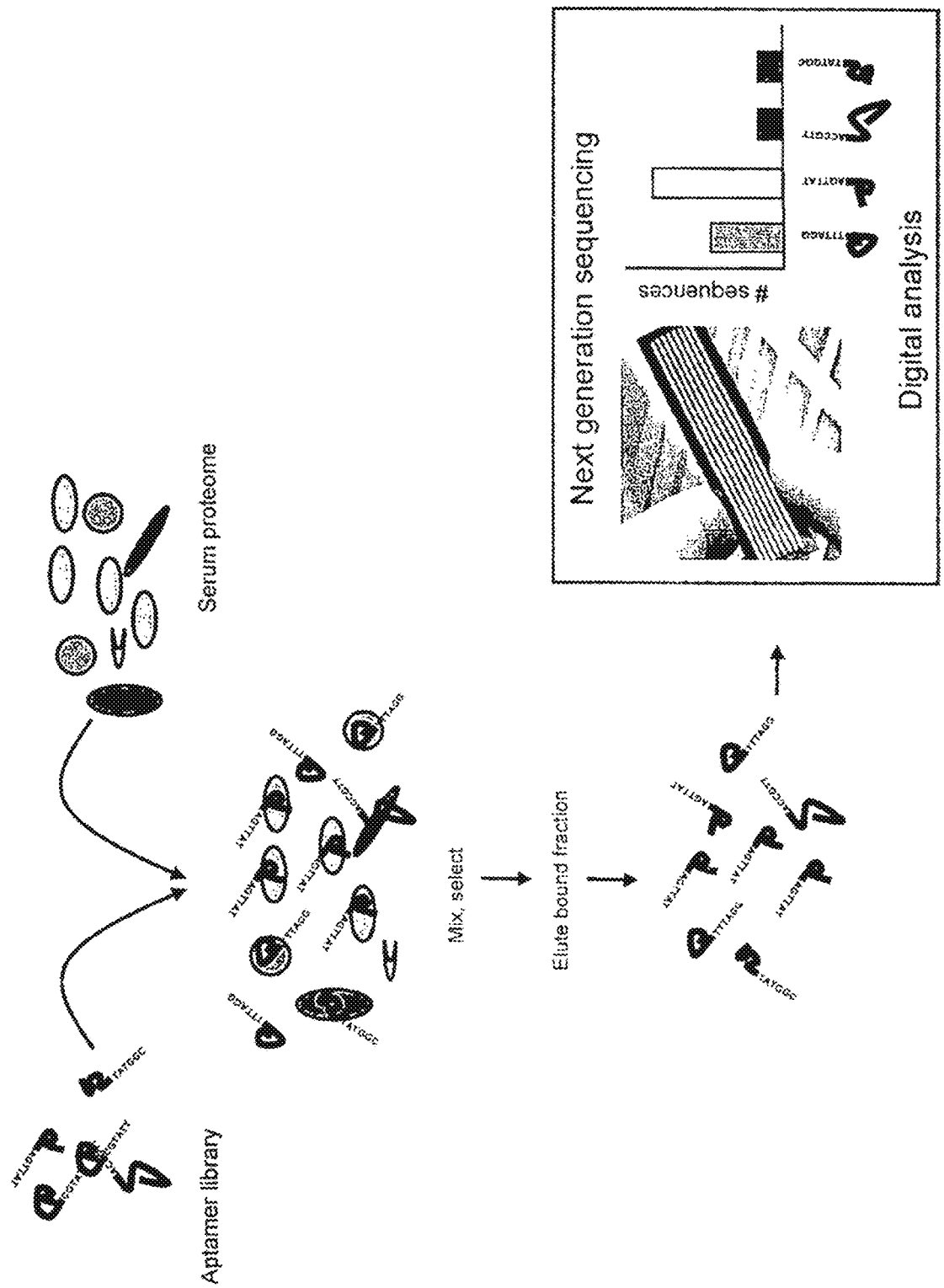

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

The invention resides in the use of an aptamer as a tag to quantify a protein, wherein the sequence of the aptamer is the tag. It has been appreciated that an aptamer has a unique sequence that may be read, for example, like a barcode. According to the present invention, it is this unique barcode that is the tag for each protein to which the barcode (aptamer) binds. By reading the barcode (sequencing the aptamer), the need for additional tags and/or labels is obviated.

In contrast with existing methods, use of the aptamer sequence as a tag allows identification and quantification of a protein using only a single molecular entity. Indeed, sequencing of an aptamer allows counting of the instances or occurrences of each distinct sequence and so allows direct quantification of the protein to which each aptamer has bound. In other words, each aptamer is a direct representation of a protein within a sample or protein mixture when an individual aptamer binds and individual protein. It will be appreciated that, by way of the method of the present invention, manipulation of the original protein or sample is minimized, thereby allowing interrogation of a protein or a mixture of proteins in as near to a natural state as is possible. In this way, a true picture of a protein or population of proteins is obtainable.

In a preferred embodiment, sequencing of the aptamers is achieved without amplification so an absolute or digital count of the aptamers by counting the occurrence of each species on a sequencing device that separates out each individual molecule prior to sequencing, for example a 'next-generation' DNA sequencer. A direct count of the occurrence of each sequence is obtained which, in turn, equates to an absolute count of the proteins to which the aptamers have bound. A subset of the sequences may be represented on the counting device which should be a representative sample of the occurrence of the given sequences in the population of molecules under study. This, again, is in contrast to current aptamer quantification methods which typically require amplification of bound tag or amplification of the aptamer molecule yielding an analogue estimate of its relative abundance (as described in US Patent Publication No. 2007-0166741). This is due to the limitations of using labels and additional tags by which the aptamers that have bound proteins are identified. As a result, quantification is proportional to the actual abundance, i.e, an analogue signal, and absolute or individual occurrences cannot be resolved.

A further advantage of using the aptamer sequence as a tag is that the sequences provide a huge range of possible tags. For example, a sequence of four bases offers 256 different combinations and thus 256 possible unique identifiers or tags. Thus, while the entire aptamer sequence may be obtained, the number of nucleotides sequenced needs only to be sufficient to identify a particular aptamer. In other words, either the whole aptamer sequence is the tag or the tag is part of the aptamer sequence.

Although the method of the present invention may be used to quantify a single protein in a sample with one aptamer sequence, a further advantage of the present invention is that the range of possible tags provided by unique sequences allows many proteins to be quantified, at the same time, in the same sample, Thus, a panel or library of known aptamer sequences may be used to quantify multiple proteins in a complex mixture and, in this way, the invention allows interrogation of complex biological samples.

Furthermore, a panel or library of aptamers may be targeted to specific proteins, in particular, proteins that are known to be present in a sample in low quantities. Since it is rarely possible to identify and quantify low abundance proteins in a sample using known methods, the present invention provides a solution for interrogating these small and, so far, elusive populations. The library or panel should ideally contain an excess of aptamer species for probing samples.

The invention may analyze a single protein (e.g., gel-excised protein) and is particularly suitable for analyzing mixtures of proteins, including complex protein mixtures. The terms "mixture of proteins" or "protein mixture" generally refer to a mixture of two or more different proteins, e.g., a composition comprising two or more different proteins.

In preferred embodiments, a mixture of proteins to be analyzed may include more than about 10, preferably more than about 50, even more preferably more than about 100, yet more preferably more than about 500 different proteins, such as, e.g., more than about 1000 or more than about 5000 different proteins. An exemplary complex protein mixture may involve, without limitation, all or a fraction of proteins present in a biological sample or part thereof.

The terms "biological sample" or "sample" as used herein generally refer to material, in a non-purified or purified form, obtained from a biological source. By means of example and not limitation, samples may be obtained from: viruses, e.g., viruses of prokaryotic or eukaryotic hosts; prokaryotic cells, bacteria or archeae, e.g., free-living or planktonic prokaryotes or colonies or bio-films comprising prokaryotes; eukaryotic cells or organelles thereof, including eukaryotic, cells obtained from in vivo or in situ or cultured in vitro; eukaryotic tissues or organisms, e.g., cell-containing or cell-free samples from eukaryotic tissues or organisms; eukaryotes may comprise protists, e.g., protozoa or algae, fungi, e.g., yeasts or molds, plants and animals, e.g., mammals, humans or non-human mammals. "Biological sample" may thus encompass, for instance, a cell, tissue, organism, or extracts thereof. A biological sample may be preferably removed from its biological source, e.g., from an animal such as mammal, human or non-human mammal, by suitable methods, such as, without limitation, collection or drawing of urine, saliva, sputum, semen, milk, mucus, sweat, faeces, etc., drawing of blood, cerebrospinal fluid, interstitial fluid, optic fluid (vitreous) or synovial fluid, or by tissue biopsy, resection, etc. A biological sample may be further subdivided to isolate or enrich for parts thereof to be used for obtaining proteins for analyzing in the invention. By means of example and not limitation, diverse tissue types may be separated from each other; specific cell types or cell phenotypes may be isolated from a sample, e.g., using FACS sorting, antibody panning, laser-capture dissection, etc.; cells may be separated from interstitial fluid, e.g., blood cells may be separated from blood plasma or serum; or the like. The sample may be applied to the method of the invention directly or may be processed, extracted or purified to varying degrees before being used.

The sample may be derived from a healthy subject or a subject suffering from a condition, disorder, disease or infection. For example, without limitation, the subject may be a healthy animal, e.g., human or non-human mammal, or an animal, e.g., human or non-human mammal, that has cancer, an inflammatory disease, autoimmune disease, metabolic disease, CNS disease, ocular disease, cardiac disease, pulmonary disease, hepatic disease, gastrointestinal disease, neurodegenerative disease, genetic disease, infectious disease or viral infection, or other ailment(s).

Preferably, protein mixtures derived from biological samples may be treated to deplete highly abundant proteins there from, in order to increase the sensitivity and performance of proteome analyses. By means of example, mammalian samples such as human serum or plasma samples may include abundant proteins, inter cilia albumin, IgG, antitrypsin, IgA, transferrin, haptoglobin and fibrinogen, which may preferably be so-depleted from the samples. Methods and systems for removal of abundant proteins are known, such as, e.g., immuno-affinity depletion, and frequently commercially available, e.g., Multiple Affinity Removal System (MARS-7, MARS-14) from Agilent Technologies (Santa Clara, California).

While the present invention has particular application to the quantification of proteins, it is to be appreciated that the invention also has an application for the quantification of other molecules, such as metabolites and the identification of potential small molecule and biological therapeutics.

In one embodiment, the present invention uses next generation polynucleotide sequencing techniques to identify and quantify aptamer tags. In this way, the present invention provides a more sensitive and efficient method of quantification, compared to currently available methods, and harnesses the large dynamic range, specificity and sensitivity offered by this genomic methodology in the field of proteomics.

Next generation polynucleotide sequencing techniques require the separation of individual molecules of DNA or RNA or other polynucleotide sequences onto a surface, such as a bead or chip, thereby creating a single molecule array of sequences. The array has a surface density that allows each molecule to be individually resolved, for example by optical microscopy. Sequencing of the polynucleotide molecules on the array allows 'digital,' i.e., absolute, counting of the sequences and, thus, direct quantification of the sequences present on the array. In some technologies, sequences may be clonally amplified once arrayed to strengthen and/or clarify the signal from each sequence. Nonetheless, quantification is obtained by counting the occurrence of sequences on the array and not the signal produced from each amplicon. Examples of suitable sequencing and quantification techniques may be found in publications such as WO 00/006770 and Branton el al (Nature Biotechnology (2008) 26 1146-1153).

Accordingly, in a preferred embodiment, quantification of the bound aptamer sequences is carried out using a single molecule array of the bound sequences. Alternatively, the aptamer sequences may be quantified on a clonal array, in which each sequence is amplified after being arrayed on a surface.

Because of the high specificity of an aptamer for its target protein, an aptamer can be used as a proxy for a protein within a mixture. After binding to its protein and subsequent elution, quantification of an aptamer via counting the frequency of its sequence on a parallel sequencing device will enable quantification of a particular protein within the sample. This will, by implication or proxy, be in a manner similar to the use of antibodies as proxies for proteins. Indeed, the distribution of aptamer sequences or tags will be representative of the distribution of the corresponding proteins in the biological population or sample from which the protein was obtained.

Furthermore, counting of clonal molecules on arrays provides an absolute number for the quantity or proportion of each aptamer tag. This is termed "digital counting" and differs from existing DNA/RNA quantification methods which rely on indirect analogue measurement of parameters such as fluorescence of an attached dye. In this way, no manipulation of the proteins or the protein mixture is required, except exposure of the aptamers under suitable conditions. In addition, digital counting is believed to be superior as it avoids many of the ambiguities and signal noise problems of analogue quantification (Smyth G K, Bioinformatics (2007) Sep 19).

In a specific embodiment and as shown in FIG. 1, a library of aptamers is screened and selected against in vitro sets of folded proteins derived from biological material e.g. serum. It will be appreciated that the library of aptamer tags may be generated by any method, including SELEX and methods described in co-pending application number EP 07020629.7.

Aptamers that do not bind proteins are removed or eluted. To achieve this, various known options are available. For example, a single protein or a complex protein sample may be immobilized on a solid support. Stringent washing may be performed to remove unbound and weak binding aptamers. Another option is the use of reversible cross-linking of the aptamer on the protein targets (photoaptamers). Non-SELEX approaches based on equilibrium capillary electrophoresis of equilibrium mixtures (ECEEM) or the non-equilibrium variant (NECEEM) may also be employed rapidly to select 'smart' aptamers with defined binding properties (Drabovich et al, Anal. Chem, (2006) 78, 3171-3178). The remaining hound aptamers are removed from their protein hosts and run through a next generation sequencer where they are sequenced and counted.

As a specific example of next generation sequencing, the bound aptamers are randomly arrayed on a surface, such as a bead or a chip. The aptamers are optionally amplified cyclically yielding groups of clonal single stranded molecules at discrete x and y coordinates on the surface or on an individual bead. After the sequences are bound to the array, a primer is added to each sequence. A DNA sequencer then executes a stepwise chemistry consisting of reagents that allow the determination of one base on each complementary sequence per cycle. In this way, a complementary sequence mirroring each bound aptamer sequence is built up. An illumination and imaging system allows this process to be photographed and, by repeating the procedure several times, the sequences of the original aptamers can be obtained. Typically such technologies are able to sequence in excess of 40-100 million fragments of DNA at up to 50 base pairs in length and these numbers are increasing rapidly. This process currently takes less than 1 to 3 days from sample preparation to sequencing output and these timescales are shortening.

It will be appreciated that other methods that fall into the category of "next generation polynucleotide sequencing" may be used and the present invention is not limited to the specific example provided. "Next generation polynucleotide sequencing" is a term generally coined to described DNA/RNA sequencing platforms that have appeared since 2004. Their common characteristic is that they use a different sequencing, chemistry from the old technology that was based on "Sanger" sequencing. The new platforms use new chemistries and generally have very high throughput and much lower costs. This has been achieved through the ability to parallelize the sequencing reactions. The new platforms typically proceed by synthesis or strand extension (building), unlike the Sanger method which works by snipping off bases (degrades). In addition, the new platforms operate on tiny numbers of clonal molecules, unlike the Sanger method which has a very large DNA sequencer molecule to base measurement ratio.

It will also be appreciated that while reference is made to DNA sequencing, the DNA sequencing technology may also be used with RNA or PNA (peptide nucleic acid) sequences. Thus, reference to next generation sequencers or sequencing encompasses DNA, RNA and PNA, as well as all other chemical variants of nucleic acid based polymers and their analogues that are suitable for use in the method of the present invention.

While a preferred embodiment of the invention uses a two dimensional array of the aptamer sequences, the invention encompasses next generation sequencing in solution and in three dimensions. For the latter, the tags may be concatenated to increase the dynamic range of the array.

A significant advantage of the present invention is that multiple aptamers directed to different proteins may be used to interrogate a complex protein mixture in one assay or experiment, thereby enabling quantification of many proteins in one sample in parallel. Such multiplexing is clearly amenable to high throughput assays such as next generation sequencing. It is believed that the power of multiple proteins to act as specific and sensitive biomarkers, when used in conjunction, far outweighs the use of single proteins since a number of biomarkers typically act in concert in a diseased state, rather than individually.

Ideally, the library of aptamer sequences comprises a pool of aptamer sequences that are specific to a single protein. Alternatively, the pool comprises aptamer sequences specific to more than one protein. For example, the library may contain aptamer sequences a1, a2 and a3 that are known to be specific to protein A. Alternatively, the library may contain aptamer sequences a1, a2 and a3, as well as b1 and b2 specific for protein B, c1 etc. While aptamer sequences a1, a2 and a3 may be specific for protein A, the invention encompasses the scenario when, for example, aptamer sequence a2 is also specific for protein B. In other words, the library of aptamers may contain sequences that are discretely specific for a protein, as well as sequences that bind to more than one protein. The latter scenario may be useful when searching for related families and groups of proteins within a mixture.

While it is preferred that the identity of the protein or molecule to which the or each aptamer binds is known, such a feature is not essential. For example, the class of protein to which an aptamer binds may be known but specific members of the class may be altered in a diseased state. The identity of proteins may be elucidated once quantification has been completed. For example, one or more specific aptamers may be assayed against a protein mixture. The aptamer(s) bind specifically to the protein of interest which may then be isolated and purified from the mixture. A significant advantage of the present invention is that actual identification of the protein biomarker need not be ascertained until the end of the interrogation process. Thus, manipulation of the protein sample is not required during interrogation.

It will be appreciated that polypeptide sequencing may be carried out by any known method. For example, art aptamer of interest may be immobilized on a column, a protein mixture flowed through the column and protein bound to the aptamer on the column analyzed using conventional MS-based proteomics.

In another embodiment, the aptamers carry unique sequence tags. In this way, once aptamers have been identified as binding to one or more proteins of interest, the tags may be removed from the aptamers and the tags are then sequenced and counted. In this way, the tags are used as an address for an aptamer and provide an alternative method of providing quantification.

It will be appreciated that the method may be used to provide a variety of solutions and answers. In particular, the method may be used to interrogate a biological sample to ascertain whether certain proteins or molecules are up- or down-regulated in a diseased state when compared to a healthy state. Because panels of aptamers may be used at the same time, the invention allows the interrogation of a raft of potential and/or known biomarkers at the same time. The use of aptamer sequences as tags, rather than indirect tags and markers such as radiolabels and antibodies, allows identification of molecules that are up- and down-regulated, as well as alterations in post-translational modifications, conformational changes, emergence of variants and the like. In this way, the canvas of possible biomarkers that can be identified is far broader than that which is possible if using currently available techniques.

Indeed, particular areas of proteome may be selectively interrogated using a focused set of aptamers. Furthermore, because aptamer sequences offer such a large range of possible tags, a number of discrete areas of the proteome may be interrogated at the same time.

In a further embodiment, an aptamer panel or pool may be challenged with a complex sample. The bound fraction may then be eluted and re-probed against a second, different sample. Free, unbound aptamers will then reflect the difference in protein abundance. In this way, changes in protein abundance can be measured, as well as the emergence of any proteins appearing in the sample as a result of a diseased or post-treatment state, for example. In these embodiments, the complex protein mixture is typically derived from a bodily fluid, such as blood, plasma or serum.

It will be appreciated that the invention may also be used to validate biomarkers. Specifically, a panel or collection of distinct aptamers may be screened against a protein sample from one or more healthy individuals and compared with protein samples taken from one or more individuals having a disease of interest.

Because many proteins may be quantified at the same time, the invention is highly amenable to high throughput analysis, thereby significantly reducing the cost and time typically required for biomarker validation.

An advantage of the present invention with respect to validation of a protein biomarker is that aptamers can be used instead of antibodies. The generation of specific antibodies is expensive and not always successful. On the other hand, it is usually possible to generate a selective aptamer to a given process and the process is far quicker and cheaper. In use, one or more aptamers specific for a particular protein of interest are assayed against a complex protein mixture. Absence of aptamer binding in a healthy sample compared to binding in a diseased sample (or vice versa) can be elucidated via counting of the aptamers. Again, no manipulation of the protein sample is necessary and no identification of proteins per se is required. In addition, multiple aptamers may be assayed against a raft of proteins of interest in one experiment.

By enabling the full complement of proteins to be interrogated, the method of the present invention may also be used to build up a picture of the conformation and abundancy of proteins in individuals. That is, to provide a profile, or map, of a patient's protein make-up. For example, a picture of Prostate Specific Antigen (PSA) may be used to establish prognosis and diagnosis of prostate cancer, as well as providing an indication of disease progression.

In another example, if a patient is found to have a certain protein variant, information about a patient's protein profile can be used for disease prognosis or susceptibility and can be used to assist with the development of individualized treatment regimens for the patient. For example, people carrying a specific mutation in their CCR5 gene produce a variant CCR5 receptor. These variant receptors do not bind HIV and so a person carrying the variant receptor has a lower chance of becoming HIV+ and progressing to AIDS as a result.

The invention may also be used to determine specificity of an aptamer for a single molecule, such as a protein, by ascertaining the variance between replicates of the same sample, as well as variance between samples obtained from different individuals.

Use of the invention also resides in diagnostics. Specifically, one or more aptamers known to identify validated biomarkers may simply be used to interrogate a bodily fluid, such as blood or serum, taken from an individual. Because the binding of an aptamer indicates the presence of a protein, a panel of aptamers may be used to identify a single or a suite of biomarker proteins that are known to be altered in an abnormal state. For example, profiling may be used to assess quantities of specific proteins against a known baseline. Examples of such uses would be use as a pregnancy test, or a test for PSA levels. In another example, sepsis is an abnormal state in which many factors are known to be up- or down-regulated according to the type of sepsis and the stage of infection.

Such a diagnostic may be in the form of a kit that includes a panel of aptamers, the binding of which indicates the presence of biomarkers known to be specific to a particular abnormal state in a biological sample derived from an individual.

In another embodiment, the invention may be used to determine disease progression. For example, the biomarker pattern in sepsis changes over the course of the infection. The identification of biomarkers as indicators of sepsis progression would greatly assist in the drawing up of appropriate treatment regimes.

The invention also allows patient profiling which, in turn, may be used to direct treatment regimes and possible prophylactic treatment. Thus, the invention provides a single platform on which a variety of outputs may be achieved.

In a yet further aspect, the present invention encompasses the use of clonal or single molecule arrays for the sequencing and counting of aptamers.

The inventors have realized that aptamers may ideally be adapted to enhance their compatibility with Next-Generation DNA sequencing platforms. Therefore, the aptamer may be enhanced to enable sequencing and identification of the aptamer using such technology platforms. Thus, from another aspect, the present invention encompasses a sequencing-enabled aptamer comprising an aptamer sequence and an adapter sequence. The adapter sequence comprises a sequence which enables attachment of the aptamer to a surface to enable sequencing of the aptamer.

The sequencing-enabled aptamer may additionally comprise a sequencing primer for sequencing of the aptamer.

Such constructs may include more than one sequencing and attachment adapters. For example, the aptamer sequence may be sandwiched between pairs of sequencing and attachment adapters annealed to each end of the aptamer sequence.

The sequencing-enabled aptamer may also comprise a label, to enable visualization of the aptamer. It will be appreciated that any suitable label may be used, including fluorescent labels and radio-labels.

Sequencing-enabled aptamers of the present invention may be used in the methods, uses and diagnostic kits described above.

The invention will now be described by way of the following non-limiting examples.

Example 1

This example is illustrated in FIG. 1 which shows the quantification of proteins in a serum sample using a library of aptamer tags. A diverse library of known aptamers is screened against a protein mixture derived from serum. The protein mixture is immobilized on a solid support and stringent washing is performed to remove unbound and weakly binding aptamers.

The remaining bound aptamers are then removed from their protein hosts and sequenced and counted on a next generation sequencer. After being arrayed, the bound aptamer sequences may be amplified by standard methods, such as PCR, to increase the clarity of the signal over background noise on the sequencer.

The output from the sequencer will be an absolute quantification of proteins present in the biological sample, as represented by the library of aptamers.

Example 2

Figure 2:
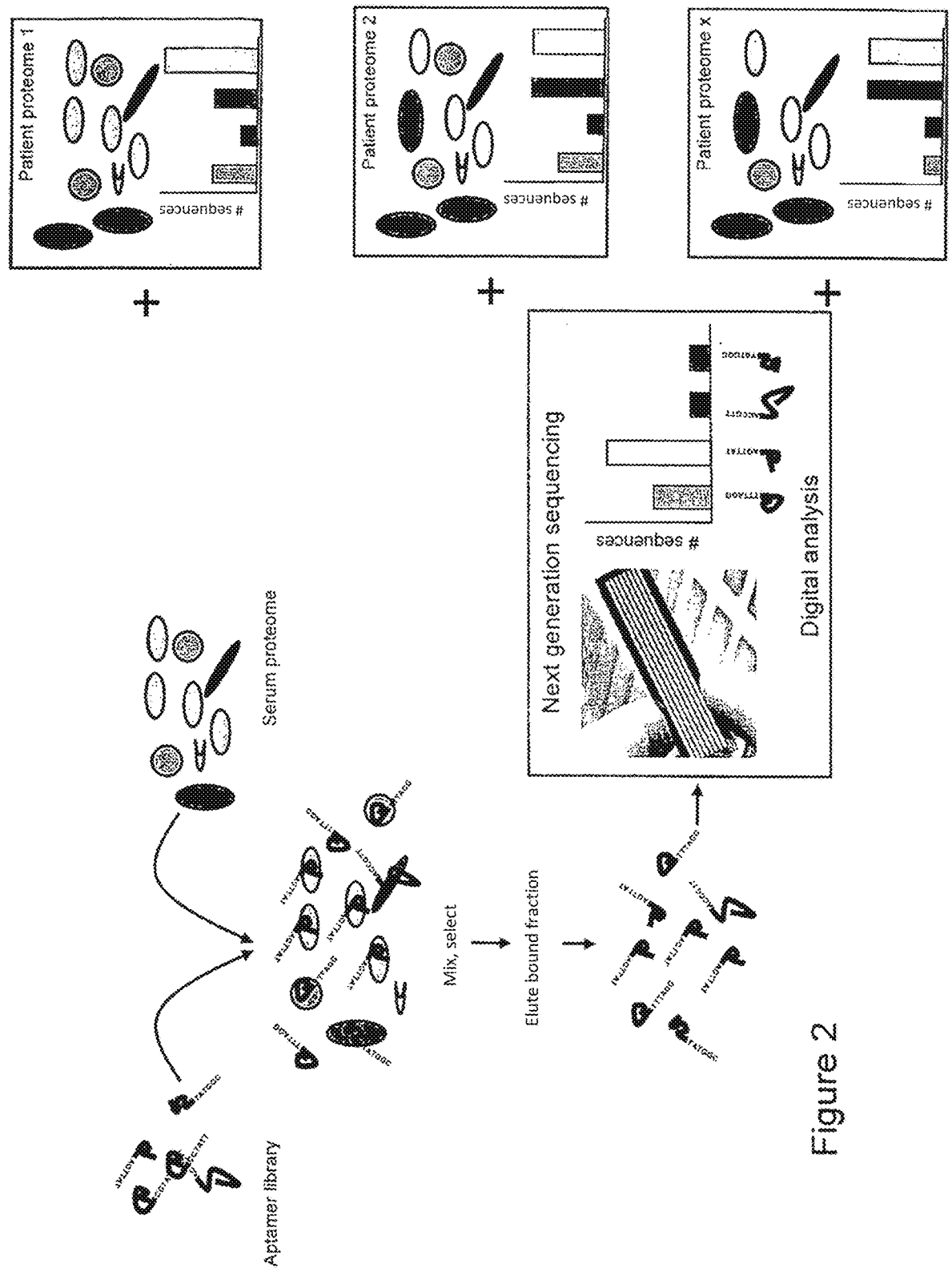

For use in biomarker discovery and as shown in FIG. 2, the library of aptamers is screened against samples derived from different individuals. A suitable number of known control, or healthy samples will also be required to establish a baseline or healthy condition. A number of samples known to represent a diseased state will also be screened. A comparison of the two populations, healthy versus diseased, will allow the identification of aptamers that show significant alternations between the two populations. Once the sequence of the or each aptamer has been elucidated, the protein to which the aptamers bind may then be identified. Identification of the protein may be by next generation sequencing techniques, or proteomic-based methods, such as chromatography and MS.

Example 3

Figure 3:
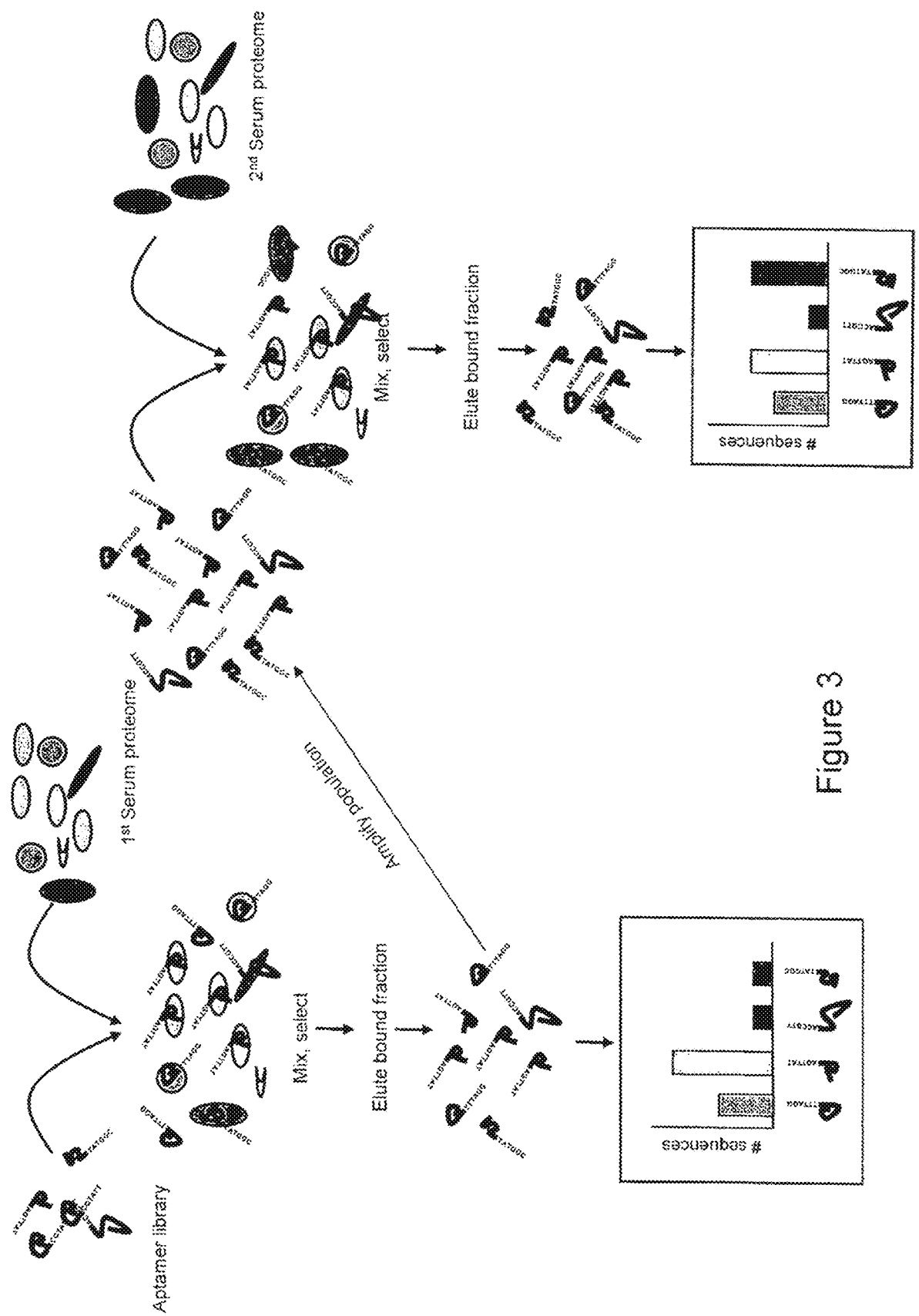

This Example describes an alternative method of the present invention and is illustrated in FIG. 3.

An aptamer library is screened against a first biological sample. As with either Example 1 or Example 2, the non-bound aptamers are removed and the remaining bound aptamers are released from their host proteins and sequenced and counted on a next generation sequencer.

The population of sequences that bind to proteins in the first sample is then screened against a second biological sample. As before, the non-bound aptamers are discarded and the remaining aptamers are sequenced and counted. If the two samples are derived from healthy subjects, any variation between the two samples may be attributed to variance within the normal population. Similarly, any variance between the outputs from two samples derived from patients known to have a particular disease may also be attributed to variance. However, any significant variance between healthy and diseased subject may be attributed to a change in the protein population as a result of the disease of interest. The aptamer sequences in which significant changes are found may then be translated to identify the protein(s) to which the aptamer(s) bind.

Example b 4

In this example, the aptamer library comprises at least one pool of aptamers specific for one protein. Equally, the panel may contain a number of pools of aptamers, where each pool is specific for a different protein.

The protein mixture may simply be a biological sample, such as blood or serum. Alternatively, the protein mixture may be obtained by enriching the biological sample for the protein fraction. In this example, care must be taken to minimize disruption to and denaturing of the protein population.

The library of known, selected aptamer sequences is screened against the protein mixture. In one example, the protein mixture is bound to a column and the panel of aptamers is allowed to flow through the column. Aptamers that do not bind are removed. Aptamers that do bind are removed from their protein hosts and sequenced and counted on a next generation sequencer.

If the protein of interest is indeed a biomarker for a diseased state, aptamers will be found in the bound fraction from the diseased sample and not in a sample derived from a healthy individual. Alternatively, the role of a protein as a biomarker may be manifest by up- or down-regulation of the protein in a diseased individual when compared to a healthy subject.

Example 5

In this example, the library of aptamers contains one or more sequences known to be specific for one or more proteins. The identity of the or each protein of interest is also known. The library may comprise a single pool specific to a single protein, or it may comprise many pools specific to an array of proteins.

The library of aptamers is screened against a biological sample derived from an individual, such as blood. The aptamer library may be held on a support and the biological sample passed over the aptamers, Any unbound proteins are removed and the aptamer:protein complexes retained. The retained aptamers are released from their protein hosts and sequenced and counted on a next generation sequencer.

The presence and quantity, or absence, of aptamers on the next generation sequencer may be used to diagnose a particular disease or predicament.

Example 6

A novel oligonucleotide aptamer was designed so that the aptamer was compatible with the Next-Generation DNA sequencing technology platform that was used.

The aptamer had an oligonucleotide sequence having three distinct regions: a) a functional aptamer region, b) an adapter region, and c) a label.

The aptamer region in this study was based on a well-studied aptamer (Wiegand et al J. Immunol. (1996) 157 221-230) having a high affinity for human Immunoglobulin-E.

The adapter region made the construct compatible with the sample preparation procedures of an Illumina GA1 Next Generation sequencer and was designed according to the manufacturer's protocols.

The label was fluorescent 6-carboxyfluorescein (FAM), the inclusion of which was to allow visualization of the construct.

The constructs were obtained by standard solid phase DNA synthesis and purified by polyacrylamide gel electrophoresis to ensure low error rates.

The construct with the FAM label will be referred to hereinafter as ProNuc1F and without the label as ProNuc1.

The constructs were used to demonstrate that:
i) such aptamer-derived single strand oligonucleotide sequences are compatible with sample preparation procedures used for Next Generation DNA sequence applications;
ii) the sequences can be sequenced using the Illumina GA1 sequencing technology, i.e. the identity of the ProNuc1 can be retrieved ("read"); and
iii) the count of whole ProNuc1 sequences, following a standard Ilumina GA1 sequencing experiment, directly correlates with the number of prepared ProNuc1 sequences spiked into a sample, thereby confirming that Next Generation sequencing can be applied to proteomics in accordance with the present invention.

Example 7

Capillary electrophoresis (CE) was used to confirm that the oligonucleotide sequence exhibits a distinct protein affinity.

Preparation of Reagents and Solutions

A stock 100 nM stock solution of ProNucF1 as prepared from dry aptamer source by diluting the DNA material in TGK buffer (tris(hydroxyamino)methane-glycine-potassium) buffer, pH 8.4. Following dilution, the aptamer stock solution was incubated at 75° C. for 10 minutes and subsequently cooled and stored in ice to ensure the absence of multimers. The heating procedure also ensures formation of the secondary structure of the aptamer.

Starting from a concentrated, 5500 nM stock solution of protein a dilution series of IgE was prepared in TGK buffer (Table 1):

TABLE I

| IgE dilution series | |
|---|---|
| Solution | Concentration (nM) |
| 1 | 20 |
| 2 | 40 |

TABLE I-continued

IgE dilution series

| Solution | Concentration (nM) |
|---|---|
| 3 | 60 |
| 4 | 100 |
| 5 | 150 |
| 6 | 200 |
| 7 | 300 |
| 8 | 1000 |
| 9 | 2000 |

The samples for CE demonstrating aptamer-protein complex formation were prepared by incubating 5 µl of the ProNucF1 stock solution with 5 µl of protein solution. A total of six replicates were prepared in this way for each protein concentration level.

All samples were incubated at room temperature for a minimum of 30 minutes and no longer than 40 minutes.

Apparatus

Separations were achieved using a Beckman PLACE 2200 CE-LIF system (Beckman-Coulter, Fullerton, CA, USA). Separations were performed using fused-silica capillaries (50 µm ID, 360 µm OD) with 40.2 cm total length, detector at 30 cm. Capillaries were pretreated by pumping 1 M NaOH, deionized $H_2O$, and buffer through the capillary for 10 min each. Between each electrophoretic separation the capillary was rinsed with base, water, and buffer again to remove any residual sample from the capillary Samples were injected using pressure for 4 s at 1 psi. The LIF detector employed the 488 nm line of a 3 mW Ar-ion laser (Beckman-Coulter) for excitation and emission was collected through a 520±10 nm filter. Data were recorded and analyzed with P/ACE software (Beckman-Coulter).

Protein-Aptamer Binding

Samples at each protein concentration level were run on the column in normal mode using the conditions described in Table 2, firstly to ensure that a protein-aptamer complex was indeed formed after incubation of each sample.

TABLE 2

Normal mode separation conditions

| Action | Duration (s) |
|---|---|
| Rinse 20 psi - 0.1M NaOH | 120 |
| Rinse 20 psi - Buffer | 120 |
| Inject 1 psi 4 - Sample | 4 |
| Inject 0.1 psi - Water | 1 |
| Separate 20 kV | 760 |
| Rinse 10 psi - Buffer | 60 |

Results

Figure 4:
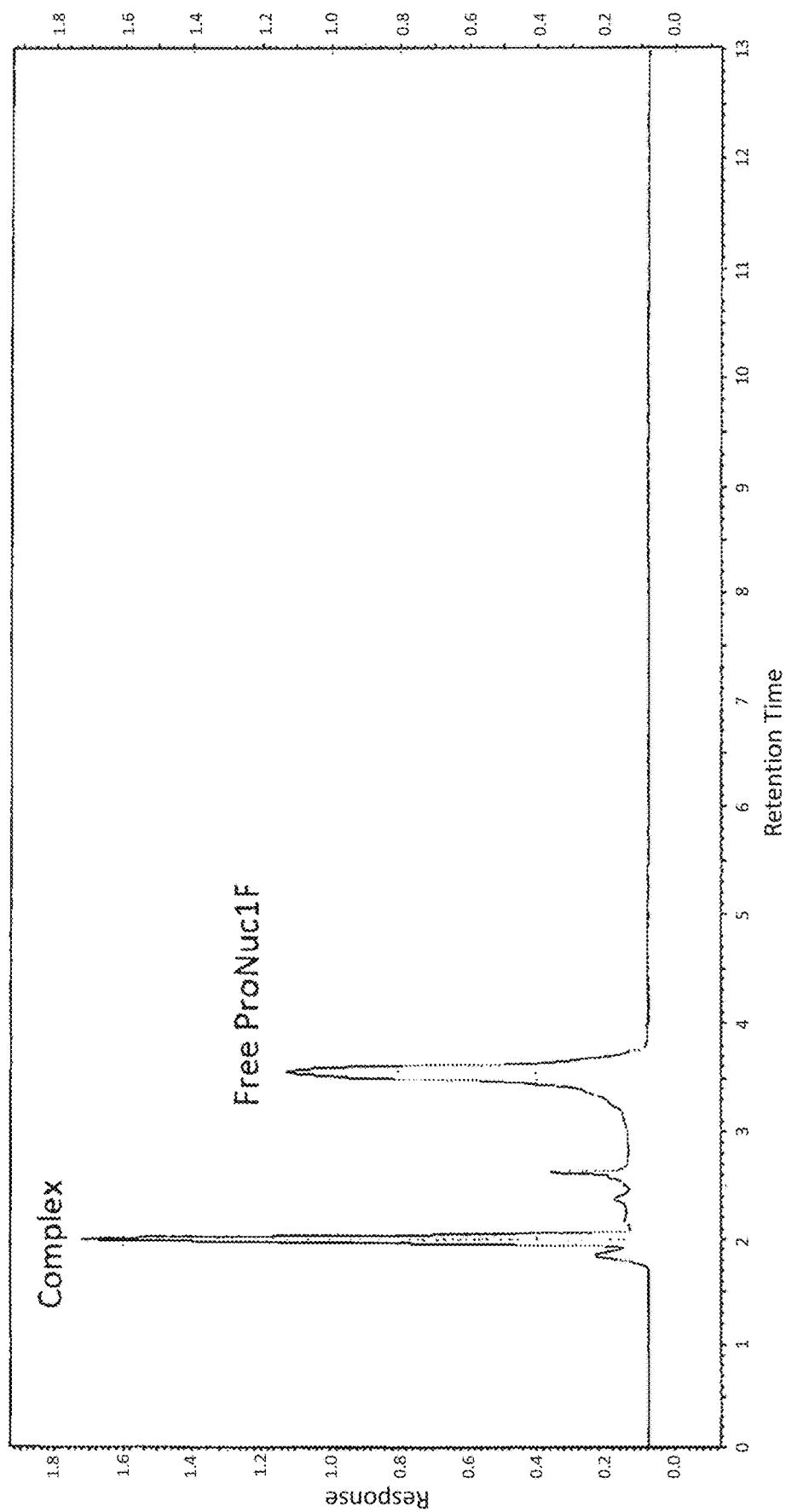
FIG. 4 is a chromatogram showing the different constituents of the mixture obtained after a 30' incubation of equal volumes of 150 nM IgE and 100 nM ProNuc1FR.

As an example, a chromatogram for normal mode injection for a sample containing 150 nM of IgE and 100 nM of ProNuc1F is shown in FIG. 4.

In order to apply the aptamer-protein complex formation for quantification purposes, the bound-aptamer fraction has to reflect the protein dilution series. To prove this, a constant amount of ProNuc1F was incubated with different protein concentrations (see above).

Figure 5:
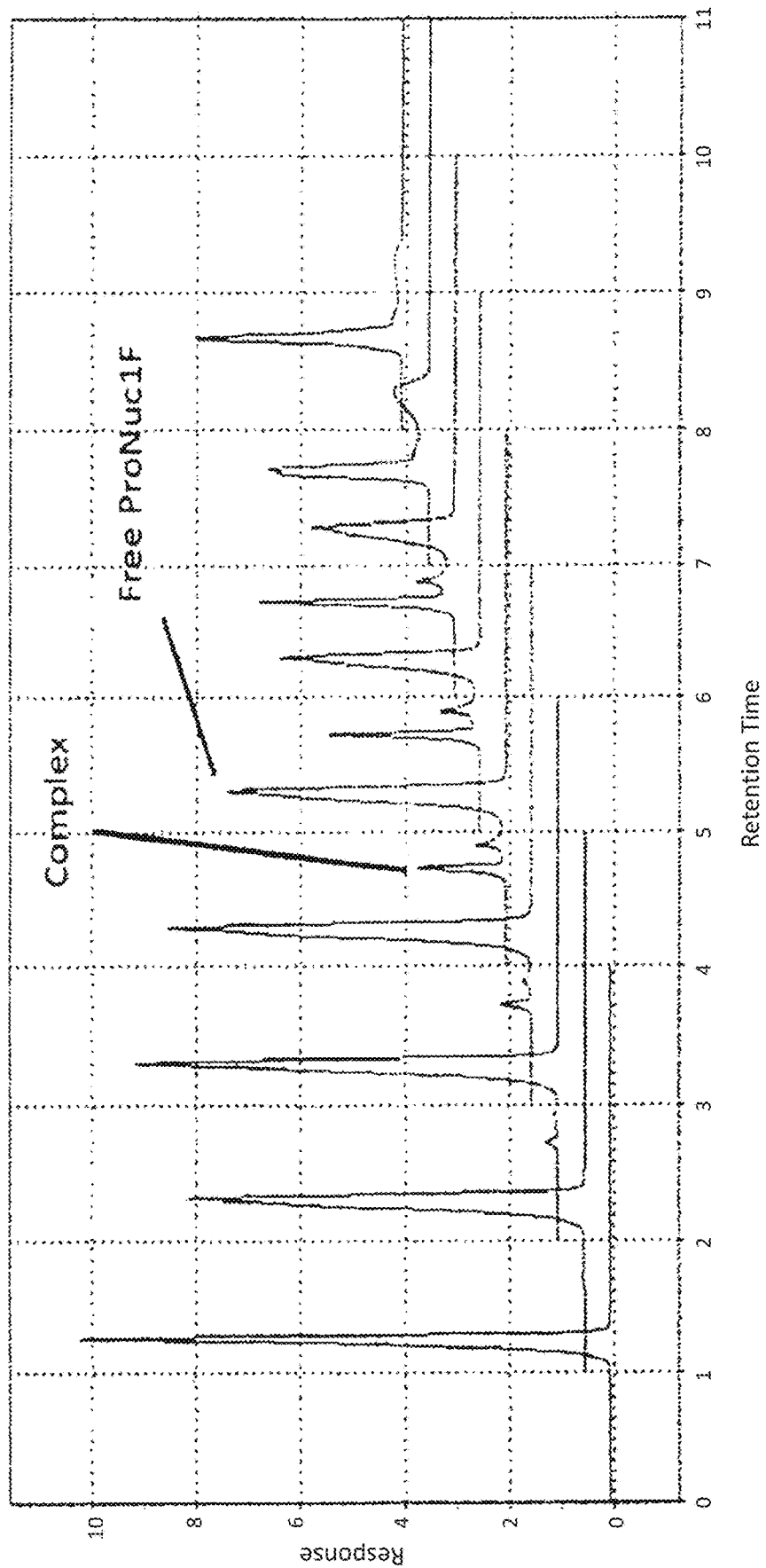
FIG. 5 shows CE-chromatograms of 0/20/40 . . . 2000 nM IgE incubated with a constant (100 nM) ProNuc1F concentration (from bottom to top).

From FIG. 5 it is clear that, with increasing protein concentration (bottom trace "0"; upper trace 5000 nM), the peak area of the aptamer-protein complex increases. Simultaneously, the signal of the free ProNuc1F decreases to the point where no free aptamer is detected (upper trace). This shows that adding an adapter sequence specific for the Next Generation Sequencing procedure to a known aptamer sequence against IgE does not impair the aptamer capabilities of ProNuc1F as ProNuc1F retains its high and selective affinity towards IgE.

Figure 6:
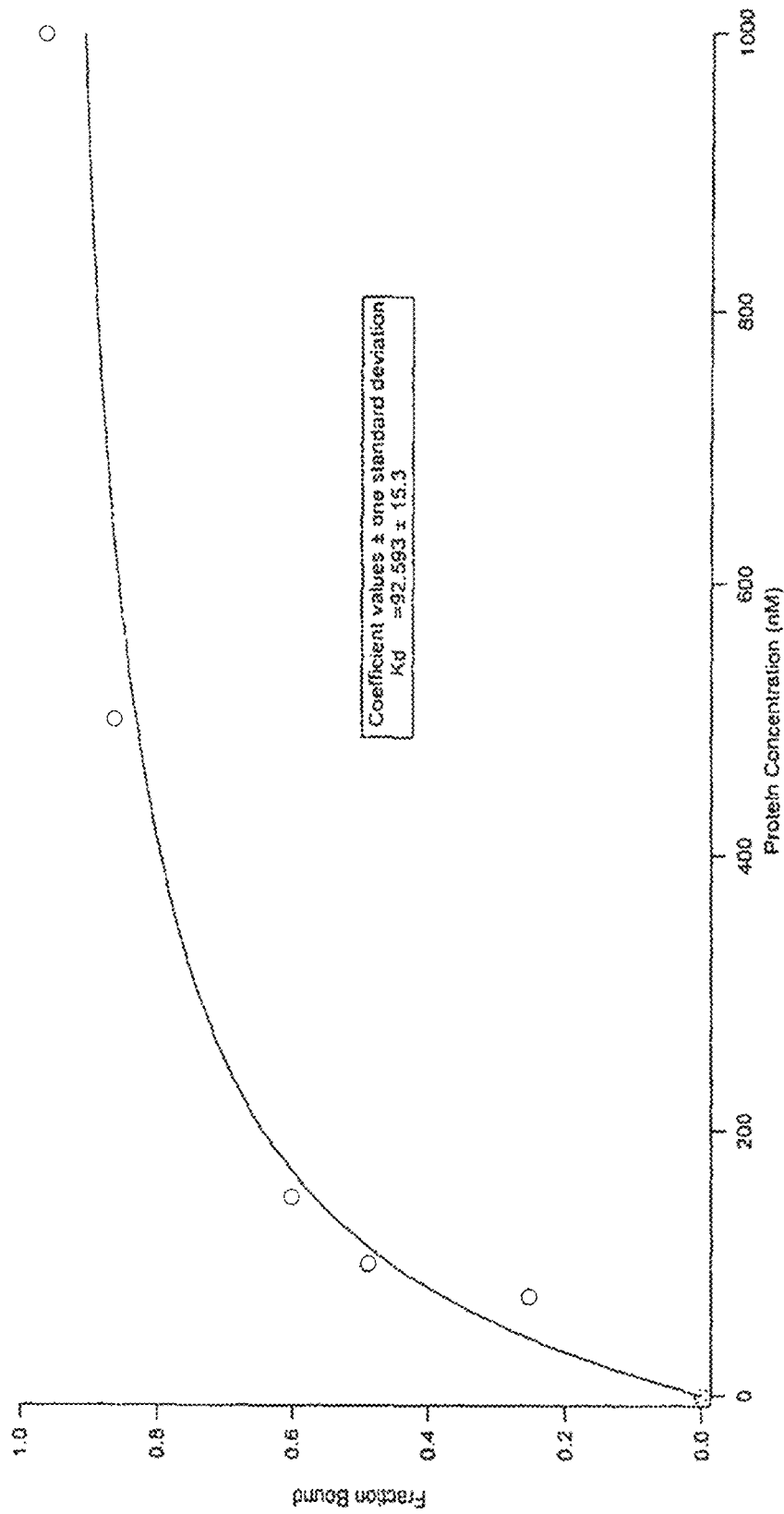
FIG. 6 is a graph showing the fraction of bound ProNuc1F plotted against changing protein concentration.

FIG. 6 shows the information in FIG. 5 translated into a graph where the "Bound ProNuc1F fraction" is plotted against the protein concentration. From this graph it can be seen that the ProNuc1F aptamer can be used to "read out" quantitative protein information. From this (and other) graphs it is also possible to deduce equilibrium dissociation constants Kd, which give insight in the affinity of ProNuc1F for IgE, i.e., between 76 and 92 nM.

Example 8

Experiments were carried out to demonstrate that the binding characteristics illustrated in the previous Example are applicable in a quantitative context, i.e. differences in protein concentration correlate with the fraction of bound aptamer (aptamer-protein complex). Selection for these aptamer-protein complexes was achieved by means of non-equilibrium capillary electrophoresis of equilibrium mixtures (NECEEM) as developed by Krylov et al (Journal of the American Chemical Society (2002) 124 13674-13675; Analytical Chemistry (2003) 75 1382-1386).

Method

An adapted sample preparation protocol was developed to allow sequencing of the functional IgE aptamer containing the added sequencing sequence (ProNuc1).

Figure 7:
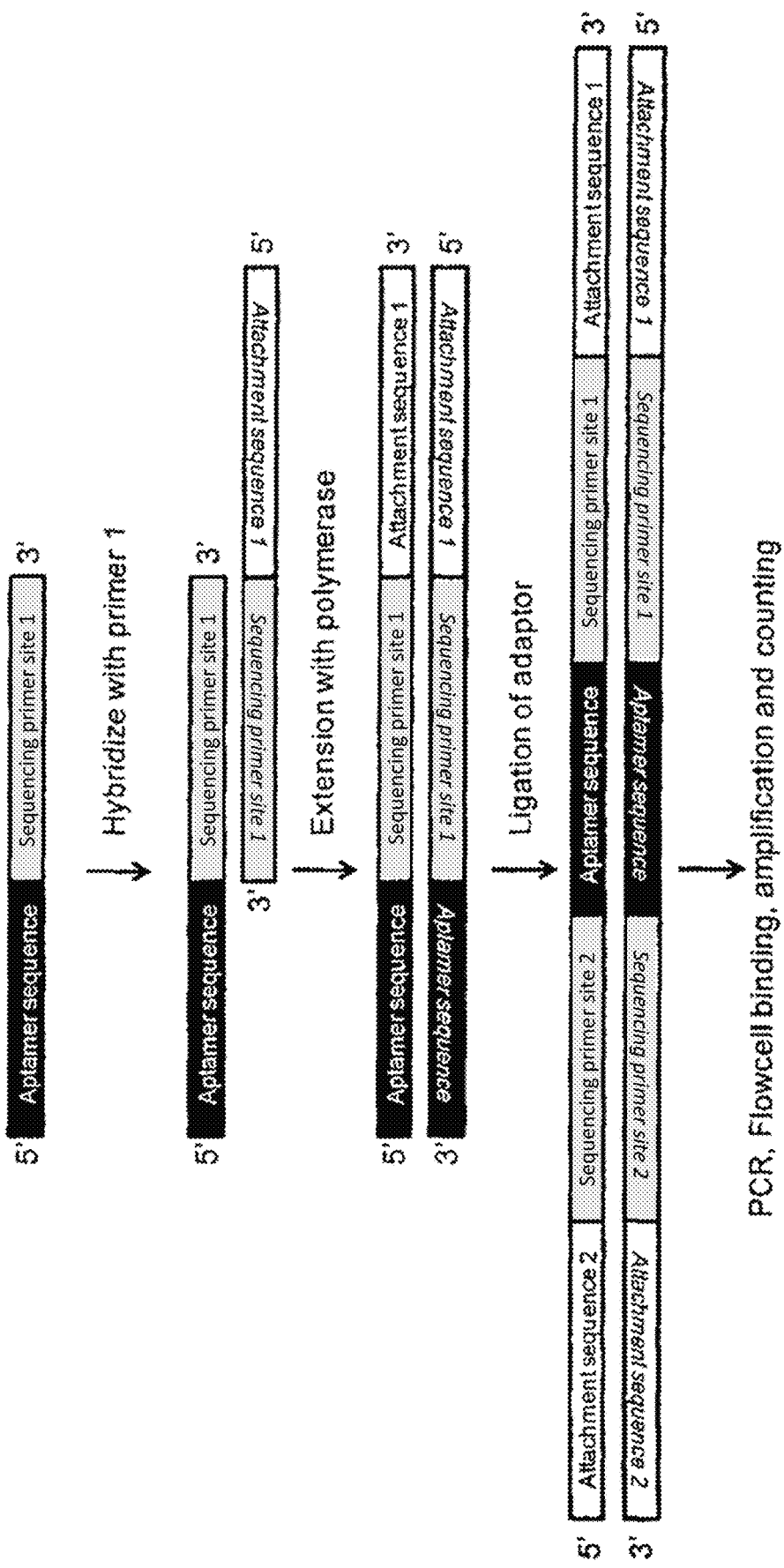
FIG. 7 is a schematic representation of the adapted sample preparation protocol for next generation sequencing of aptamers.

FIG. 7 outlines the different steps in the sample preparation protocol. After the annealing of primer 1 on Sequencing primer site 1, a double stranded molecule was formed by extension with Taq polymerase. An adaptor was ligated to the double stranded molecule generating the full molecule.

The IgE aptamer sequence used in this study was a single stranded oligonucleotide with Sequencing Primer Site 1 at its 3' end. In order to make the complementary strand, a tailed primer was annealed with primer 1 and extension was performed using Taq polymerase.

The recipe for this reaction is shown in Table 3:

TABLE 3

Extension reaction

| Component | Amount |
|---|---|
| 10 µM Pronuc1 | 2 µl |
| 10 µM Primer 1 | 5 µl |
| 2.5 mM dNTPs | 4 µl |
| 10x Taq polymerase buffer | 5 µl |
| 50 mM $MgCl_2$ | 2 µl |
| Taq polymerase | 0.5 µl |
| Water | 31.5 µl |

The reaction was mixed and heated to 94° C. for 2 minutes, followed by controlled cooling to 60° C. and incubation at 72° C. for 10 minutes. Reaction products were cleaned using a Qiagen MinElute column, following the manufacturer's instructions, and eluting in 141 EB buffer.

20 µl each of a 100 µM solution of ProAd1 and ProAd2 adapters were annealed together in a total volume of 50 µl 10 mM Tris-HCl pH 8.3 by heating to 94° C. for 2 minutes and controlled cooling to room temperature. ProAd1 and ProAd2 are synthesized oligonucleotides that are derived from the Illumina GA1 kit.

The mixture used is shown in Table 4:

TABLE 4

| Adapter reaction | |
| --- | --- |
| | Amount |
| Ds aptamer | 10 µl |
| 2x DNA Illumina ligase buffer | 25 µl |
| Annealed adapter oligo mix | 10 µl |
| Illumina DNA ligase | 5 µl |

Reactions were mixed and incubated for 15 minutes at room temperature before gel electrophoresis in 2% agarose. The appropriately-sized band was excised from the gel and the DNA was extracted and amplified following the standard Illumina enrichment PCR protocol.

PCR amplicons were quantified using an Agilent Bioanalyzer 2100 and sequencing reactions were prepared by adding these amplified aptamers to a constant quantity of PhiX, with the intention of generating the Illumina GA1 cluster numbers/tile given in Table 5, to produce a 2× dilution series. Lane 4 is PhiX with no added aptamer and serves as a control lane.

For the avoidance of doubt, PhiX refers to the circular genome of the double stranded DNA PhiX 174 bacteriophage which consists of 5386 nucleotides. In this study, the genome was processed according to the Illumina GA1 sequencing protocol to serve as normalization for the sequence load in the different lanes.

A single end flowcell was prepared and sequenced on an Illumina GA1 in accordance with the manufacturer's instructions.

TABLE 5

Actual ProNuc1 and PhiX sequence numbers used ner tile for the eight different lanes on the Illumina GA1 flowcell.

| Lane | ProNuc1/tile | ProNuc1/lane | PhiX |
| --- | --- | --- | --- |
| 1 | 5000 | 1500000 | 20,000 |
| 2 | 2500 | 750000 | 20,000 |
| 3 | 1250 | 375000 | 20,000 |
| 4 | 0 | 0 | 20,000 |
| 5 | 625 | 187500 | 20,000 |
| 6 | 312 | 93600 | 20,000 |
| 7 | 156 | 46800 | 20,000 |
| 8 | 78 | 23400 | 20,000 |

A lane consists of around 300 tiles.

Results

Figure 8:
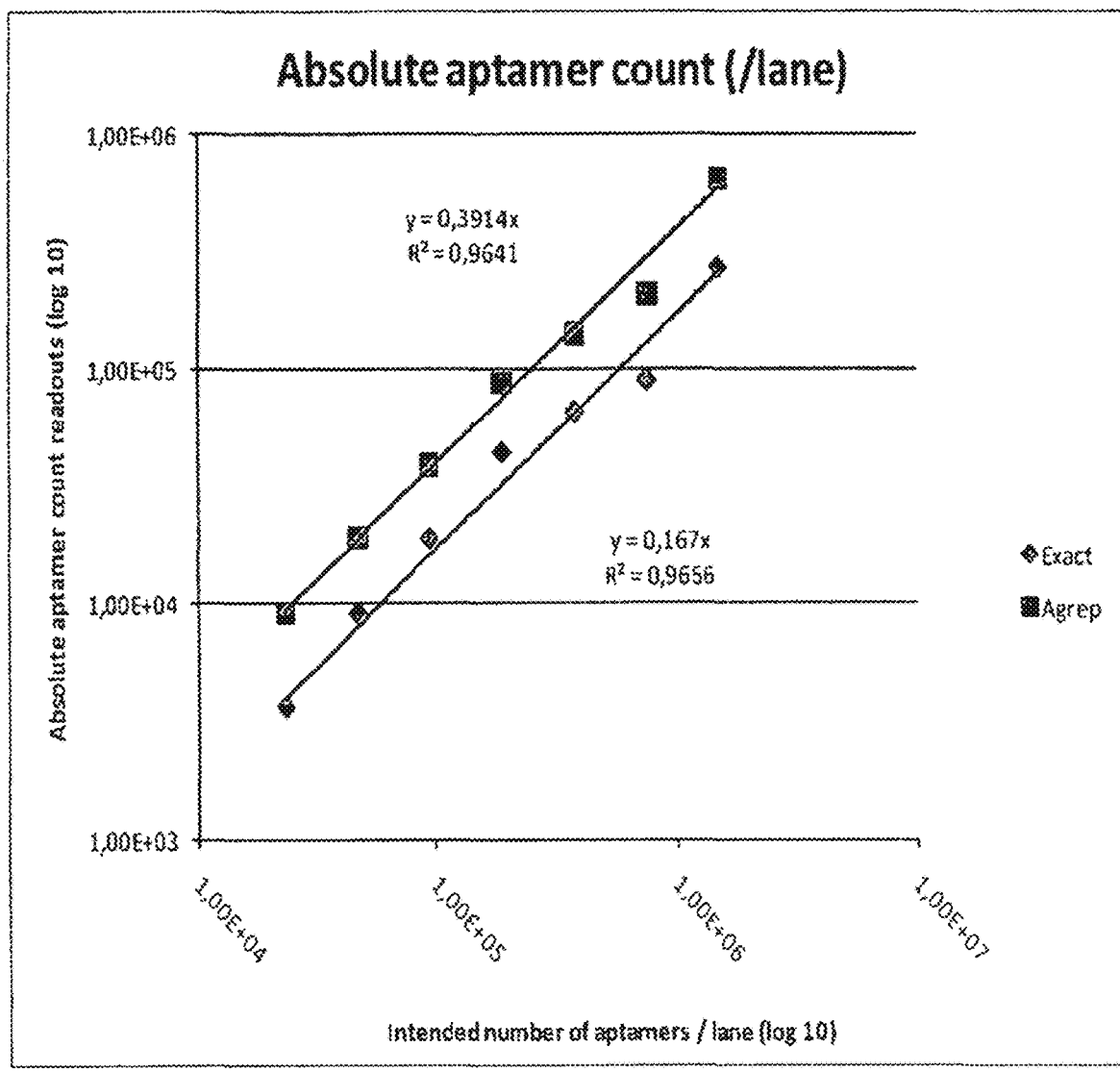
FIG. 8 is a plot showing absolute counts of IgE aptamer sequences retrieved using two different analysis methods.

Sequencing data was processed according to the manufacturer's instructions. For data analysis, different strategies were applied to evaluate the sequence read outs obtained in the different lanes: a) a search for exact matches to the aptamer sequence (exact); b) a search which allows for up to 3 amplification/sequencing errors (Agrep). It is clear that other processing methods can also be applied. FIG. 8 plots the absolute numbers of IgE aptamers counted in the different lanes by looking for exact matches/matches with up to three errors retrieved in the different lanes, i.e. an exact aptamer sequence count and an error-tolerant aptamer sequence count (Agrep). The values at the X-axis correspond to the lane readouts of lanes 8 down to 1 (control lane 4 is excluded; see Table 5).

Figure 9:
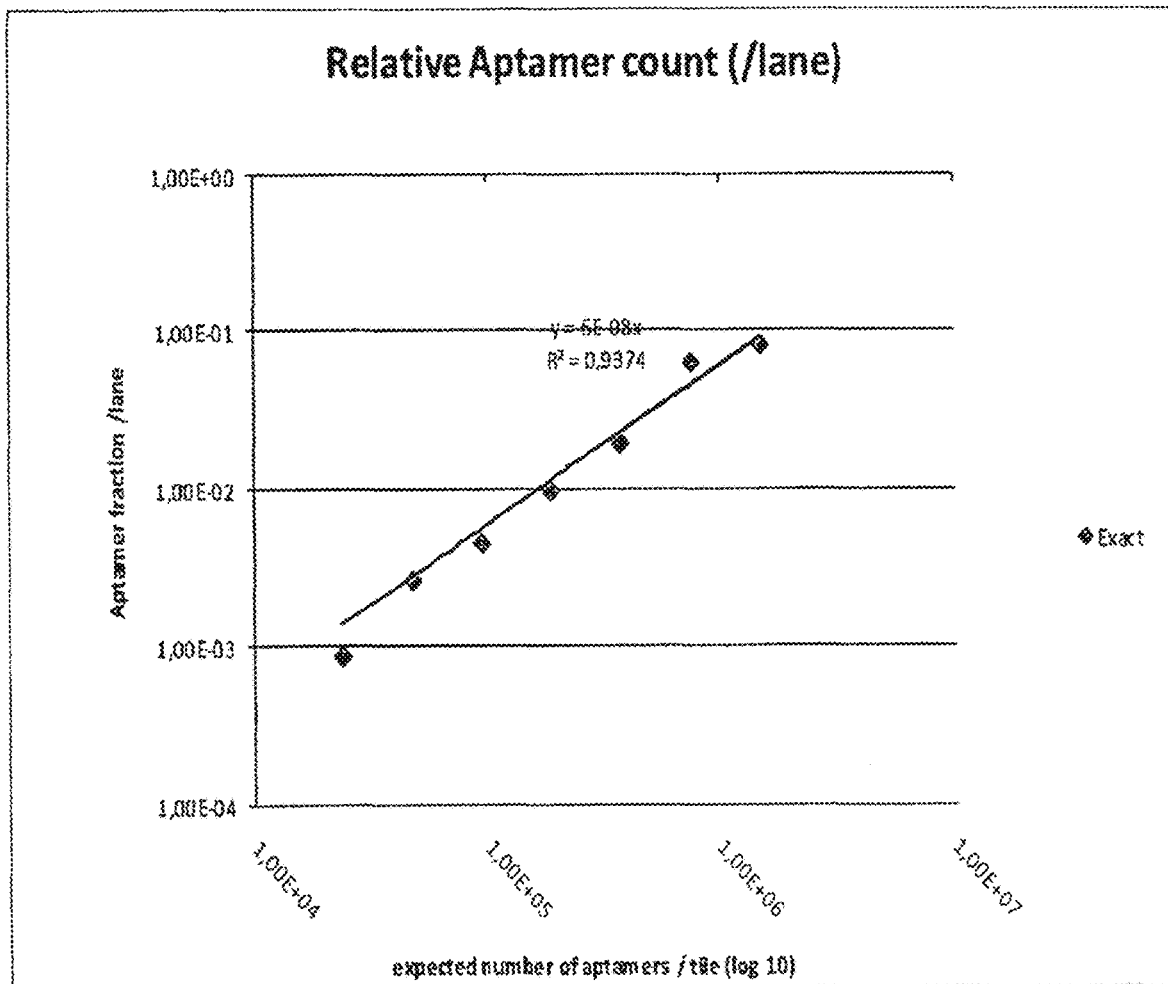
FIG. 9 is a plot showing the fraction of IgE aptamer sequences present in a mixture of sequences counted by Next Generation sequencing plotted against the number of sequences spiked in a mixture of irrelevant (PhiX) sequences.

In contrast, FIG. 9 plots the fraction of IgE aptamers counted by looking for exact matches in the total sequences obtained against the number of aptamers spiked in the PhiX sequence mixture. In both cases a strong linear correlation is shown confirming, the use of Next Generation sequencing to quantify aptamers.

The above data shows that, when following a standard Illumina GA1 sequencing protocol, the count of whole ProNuc1 sequences correlates directly with the number of prepared ProNuc1 sequences spiked into the sample, thereby confirming that Next Generation sequencing can be used for quantification in accordance with the present invention.

Furthermore, the data show that the prepared ProNuc1 sequences can be sequenced using Next Generation sequencing, technology. In other words the identity of the ProNuc1 can be retrieved ("read").

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for identifying biomarkers of disease states and/or drug treatments, the method comprising:
    (a) combining a biological sample, or a derivative thereof, with a plurality of aptamers and allowing members of the plurality of aptamers to bind to their target molecules in the biological sample;
    (b) separating members of the plurality of aptamers that bound target molecules in step a) from members of the plurality of aptamers that did not bind target molecules in step a);
    (c) using next generation sequencing techniques to sequence at least part of each of the members of the plurality of aptamers that bound the target molecules in step b) to identify and/or quantify each of the bound aptamers;
    (d) determining the identity of the target molecules of the bound aptamers and generating a profile of the target molecules;
    (e) comparing the profile of the target molecules with a control profile from a control or baseline sample; and
    (f) identifying target molecules whose occurrence or expression levels are altered between the biological sample and the control or baseline sample, thereby identifying biomarkers of disease states and/or drug treatments.

2. The method of claim 1, wherein the target molecules of the aptamers comprise proteins.

3. The method of claim 1, wherein the identity of the target molecules of the aptamers is known.

4. The method of claim 1, wherein the target molecules are identified by proteomics-based analysis.

5. The method of claim 4, wherein the proteomics-based analysis is high performance liquid chromatography (HPLC) or mass spectrometry (MS).

6. The method of claim 1, wherein the sequence of the members of the plurality of aptamers is known.

7. The method of claim 1, wherein each unique aptamer sequence carries a unique tag.

8. The method of claim 7, wherein the tag is the sequence of each unique aptamer.

9. The method of claim 7, wherein the tag is part of the sequence of each unique aptamer.

10. The method of claim 1, wherein the next generation sequencing is carried out on a single molecule array or a clonal single molecule array.

11. The method of claim 1, wherein the method further comprises disassociating the bound aptamers and molecules separated in step b) prior to step c).

12. The method of claim 1, wherein the method further comprises amplifying the plurality of aptamers in step b) prior to step c).

13. The method of claim 1, wherein the plurality of aptamers comprises different member sequences that each bind to a same target molecule.

14. The method of claim 1, wherein the plurality of aptamers comprises different panels of aptamer sequences that each bind to a different target molecule.

15. The method of claim 1, wherein the members of the plurality of aptamers comprise DNA, RNA or both.

16. The method of claim 15, wherein the members of the plurality of aptamers are between about 30 and about 60 bases.

17. The method of claim 1, wherein the control sample is a biological sample obtained from a healthy individual.

18. The method of claim 1, wherein the control sample is a biological sample obtained from an individual known to have cancer, or an individual after drug treatment.

19. The method of claim 1, further comprising the steps of:
 (i) adding an adapter sequence to each of the members of the plurality of aptamers that bound the target molecules in step b), wherein the adapter sequence comprises an attachment sequence for attachment of the aptamers to a surface; and
 (ii) attaching the members of the plurality of aptamers comprising an adapter sequence from step c) to a surface.

20. The method of claim 1, wherein the biological sample is blood, tissue biopsy or resection.

* * * * *